(12) United States Patent
Kuck et al.

(10) Patent No.: US 7,699,788 B2
(45) Date of Patent: Apr. 20, 2010

(54) NONINVASIVE EFFECTIVE LUNG VOLUME ESTIMATION

(75) Inventors: Kai Kuck, Hamburg (DE); Joseph Orr, Park City, UT (US); Lara Brewer, Bountiful, UT (US)

(73) Assignee: RIC Investments, LLC., Wilmington, DE (US)

( * ) Notice: Subject to any disclaimer, the term of this patent is extended or adjusted under 35 U.S.C. 154(b) by 1501 days.

(21) Appl. No.: 10/973,815

(22) Filed: Oct. 25, 2004

(65) Prior Publication Data
US 2005/0124907 A1    Jun. 9, 2005

Related U.S. Application Data

(63) Continuation-in-part of application No. 10/121,219, filed on Apr. 11, 2002, now Pat. No. 6,955,651, which is a continuation-in-part of application No. 09/510,702, filed on Feb. 22, 2000, now Pat. No. 6,540,689.

(51) Int. Cl.
   *A61B 5/00* (2006.01)
(52) U.S. Cl. .............. 600/532; 600/529
(58) Field of Classification Search ........ None
   See application file for complete search history.

(56) References Cited

U.S. PATENT DOCUMENTS

| | | |
|---|---|---|
| 4,221,224 A | 9/1980 | Clark |
| 4,307,730 A | 12/1981 | Korn |
| 4,363,327 A | 12/1982 | Clark |
| 4,418,701 A | 12/1983 | Luijpers |
| 4,463,764 A | 8/1984 | Anderson et al. |
| 5,060,656 A | 10/1991 | Howard |
| 5,069,220 A | 12/1991 | Casparie et al. |
| 5,117,674 A | 6/1992 | Howard |
| 5,178,155 A | 1/1993 | Mault |
| 5,285,794 A | 2/1994 | Lynch |
| 5,299,579 A | 4/1994 | Gedeon et al. |
| 5,402,796 A | 4/1995 | Packer et al. |

(Continued)

FOREIGN PATENT DOCUMENTS

DE    28 49 217 A1    5/1980

(Continued)

OTHER PUBLICATIONS

H. Blomquist et al., *A Non-Invasive Technique for Measurement of Lung Perfusion*, Intensive Care Medicine 1986; 12:172.

(Continued)

*Primary Examiner*—Robert L Nasser

(57) ABSTRACT

Methods for noninvasively measuring, or estimating, functional residual capacity or effective lung volume include obtaining carbon dioxide and flow measurements at or near the mouth of a subject. Such measurements are obtained during baseline breathing and during and shortly after inducement of a change in the subject's effective ventilation. The obtained measurements are evaluated to determine the amount of time required for exhaled carbon dioxide levels to return to normal—effectively an evaluation of carbon dioxide "washout" from the subject's lungs. Conversely, carbon dioxide and flow measurements may be evaluated to determine the amount of time it takes carbon dioxide to "wash in," or reach peak levels within, the lungs of the subject following the change in the subject's effective ventilation. Apparatus for effective such methods are also disclosed.

15 Claims, 3 Drawing Sheets

U.S. PATENT DOCUMENTS

| | | | |
|---|---|---|---|
| 5,540,233 | A | 7/1996 | Larsson et al. |
| 5,632,281 | A | 5/1997 | Rayburn |
| 5,836,300 | A | 11/1998 | Mault |
| 5,957,128 | A | 9/1999 | Hecker et al. |
| 5,971,934 | A | 10/1999 | Scherer et al. |
| 6,102,868 | A | 8/2000 | Banner et al. |
| 6,119,550 | A | 9/2000 | Wilson |
| 6,139,506 | A | 10/2000 | Heinonen |
| 6,217,524 | B1 | 4/2001 | Orr et al. |
| 6,227,196 | B1 | 5/2001 | Jaffe et al. |
| 6,302,851 | B1 | 10/2001 | Gedeon |
| 6,306,098 | B1 | 10/2001 | Orr et al. |
| 6,402,697 | B1 * | 6/2002 | Calkins et al. ............... 600/532 |
| 6,544,191 | B2 | 4/2003 | Koch et al. |
| 6,648,832 | B2 * | 11/2003 | Orr et al. ..................... 600/532 |
| 2002/0183643 | A1 | 12/2002 | Kuck et al. |
| 2003/0023162 | A1 | 1/2003 | Baumgardner et al. |

FOREIGN PATENT DOCUMENTS

| | | |
|---|---|---|
| WO | WO 96/24285 | 8/1996 |
| WO | WO 98/12963 | 4/1998 |
| WO | PCT/US00/24044 | 1/2000 |

OTHER PUBLICATIONS

R.J. Bosman et al, *Non-Invasive Pulimonary Blood Flow Measurement by Means of $CO_2$ Analysis of Expiratory Gases*, Intensive Care Medicine 1991, 17:98-102.

A. Gedeon, *Non-Invasive Pulmonary Blood Flow for Optimal Peep*, ICOR AB, Ulvsundavagen 178 B, S-161 30 Bromma, Sweden, pp. 49-58.

Capek, J.M., *Noninvasive Measurement of Cardiac Output Using Partial $CO_2$ Rebreathing* [Dissertation], Rensselaer Polytechnic Institute (1988) 28:351 p. (due to large number of pages, only table of contents and abstract have been copied).

Capek, J.M., et al., *Noninvasive Measurement of Cardiac Output Using Partial $CO_2$ Rebreathing*, IEEE Trans. Biomed. Eng. (1988) 35(9):653-61.

Davies, Gerald G., et al., *Continuous Fick cardiac output compared to thermodilution cardiac output*, Critical Care Medicine (1986) 14(10):881-85.

Elliot, C. Gregory, et al., *Complications of Pulmonary Artery Catheterization in the Care of Critically Ill Patients*, Chest (1979) 76:647-52.

Fick, A., *Über die Messung des Blutquantums in den Herzventrikeln*, Sitzungsbericht der Physikalisch-Medizinischen Gesellschaft zu Würzburg (1870) 36 (2 pages).

Gama de Abreu, Marcelo, et al., *Measurement of Pulmonary Capillary Blood Flow for Trending Mixed Venous Blood Oxygen Saturation and Oxygen Delivery*, Crit. Care Med. (1998), vol. 26, No. 1 (Suppl.), A106, Abstract #238, (1 page).

Gama de Abreu, Marcelo, et al., *Is the Partial $CO_2$ Rebreathing Technique a Useful Tool for Trending Pulmonary Capillary Blood Flow During Adjustments of Peep?*, Crit. Care Med. (1998), vol. 26, No. 1 (Suppl.), A106, Abstract #237, (1 page).

Gama de Abreu, et al., *Partial carbon dioxide rebreathing: A reliable technique for noninvasive measurement of nonshunted pulmonary capillary blood flow*, Crit. Care Med. (1997) 25(4):675-83.

Gedeon, A., et al., *Noninvasive Cardiac Output Determined with a New Method Based on Gas Exchange Measurements and Carbon Dioxide Rebreathing: A Study in Animals/Pigs*, J. Clin. Monit. (1992) 8(4):267-78.

Gedeon, A., et al., *A new method for noninvasive bedside determination of pulmonary blood flow*, Med. & Biol. Eng. & Comput. (1980) 18:411-418.

Guyton, A.E., et al., *Measurement of cardiac output by the direct Fick method*, In: Cardiac output and its regulation, W.B. Saunders Company (1973) 21-39.

Kyoku, I., et al. *Measurement of cardiac output by Fick method using $CO_2$ analyzer Servo*, Kyobu Geka. Japanese Journal of Thoracic Surgery (1988) 41(12):966-70.

Lynch, J., et al., *Comparison of a modified Fick method with thermodilution for determining cardiac output in critically ill patients on mechanical ventilation*, Intensive Care Med. (1990) 16:248-51.

Mahutte, C. Kees, et al., *Relationship of Thermodilution Cardiac Output to Metabolic Measurements and Mixed Venous Oxygen Saturation*, Chest (1993) 104(4):1236-42.

Miller, D.M., et al., *A Simple Method for the Continuous Noninvasive Estimate of Cardiac Output Using the Maxima Breathing System. A Pilot Study* Anaesth. Intens. Care (1997) 25(1):23-28.

Österlund, B., et al., *A new method of using gas exchange measurements for the noninvasive determination of cardiac output: clinical experiences in adults following cardiac surgery*, Acta Anaesthesiol Scand (1995) 39:727-32.

Sackner, Marvin A., *Measurement of cardiac output by alveolar gas exchange*, Handbook of Physiology~The Respiratory System IV, Chapter 13, 233-55.

Spalding, H. K., et al., *Carbon Dioxide ($CO_2$) Elimination Rate Accurately Predicts Cardiac Output*, Anesthesiology (1997) 87(3A) (1 page).

Sprung, Charles L., et al., *Ventricular Arrhythmias During Swan-Ganz Catheterization of the Critically Ill*, Chest (1981) 79:413-15.

Taskar, V., et al., *Dynamics of Carbon Dioxide Elimination Following Ventilator Resetting*, Chest (1995) 108:196-202.

Winkler, Tilo, et al., *Pulmonary Capillary Blood Flow by Partial $CO_2$ Rebreathing: A Simulation Study Using a Bicompartmental Model of Gas Exchange*, Crit. Care Med. (1998), vol. 26, No. 1 (Suppl.), A105, Abstract #234, (1 page).

Kuck et al., Noninvasive Partial $CO_2$ Rebreathing Estimates Cardiac Output and Functional Residual Capacity (FRC), Anesthesiology, University of Utah Health Sciences Center, Utah, Oct. 26, 2004, (3 pages).

Brewer et al., Novel Functional Residual Capacity Measurement Technique Based on Partial $CO_2$ Rebreathing Signals, Anesthesiology, University of Utah Health Sciences Center, Utah, Oct. 25, 2004, (3 pages).

Fretschner et al., A Simple Method to Estimate Functional Residual Capacity in Mechanically Ventilated Patients, Intensive Care Medicine, Switzerland, (1993) vol. 19, pp. 372-376.

Allen et al., Respiratory Mechanics in Infants: Physiology Evaluation in Health and Disease, Am Rev Dis (1993), vol. 147, pp. 474-496.

Beck et al., Variance of Ventilation During Exercise, University of Minnesota, J Appl Physiol (2001), vol. 90, pp. 2151-5156.

Shrake et al., Body Plethysmography, AARC Clinical Practice Guideline, Respiratory Care (1994) vol. 39 pp. 1184-1190.

Pulmonary Maneuvers System, Harvard Apparatus, Respiratory Mechanics, 1 page.

Morris, The Open Circuit Nitrogen Washout Technique for Measuring the Lung Volume in Infants: Methodological Aspects, department of Pediatrics, University of Arkansas, Thorax (1999) vol. 54, pp. 790-795.

Schibler et al., Measurement of Functional Residual Capacity in Rabbits and Children Using an Ultrasonic Flow Meter, Pediatric Intensive Care Unit, Royal Children's Hospital, Australia (2001) vol. 49, pp. 581-588.

Lung Function Fundamentals, http://www.anaesthetist.com/icu/organs/lung/lungfx.htm, (2004), 20 pages.

Plewes et al., Amount and Rates of $CO_2$ Storage in Lung Tissue, State University of New York, Respiration Physiology (1972) vol. 28, pp. 359-370.

Gedeon et al., Pulmonary Blood Flow (Cardiac Output) and the Effective Lung Volume Determined From a Short Breath Hold Using the Differential Fick Method, Journal of Clinical Monitoring and Computing (2002), vol. 17, pp. 313-321.

European Search Report, Feb. 10, 2006, 4 pages.

* cited by examiner

NONINVASIVE EFFECTIVE LUNG VOLUME ESTIMATION

CROSS-REFERENCE TO RELATED APPLICATION

This application claims the benefit of and is a continuation-in-part of application Ser. No. 10/121,219, filed on Apr. 11, 2002, now U.S. Pat. No. 6,955,651 issued on Oct. 18, 2005, which is a continuation-in-part of application Ser. No. 09/510,702, filed on Feb. 22, 2000 and issued on Apr. 1, 2003 as U.S. Pat. No. 6,540,689.

BACKGROUND OF THE INVENTION

1. Field of the Invention

The present invention relates generally to techniques for determining functional residual capacity (FRC), the volume of gases that remain within a subject's lungs following exhalation, or, more broadly, the effective lung volume (ELV) of the subject, which includes gases that have diffused into the lung tissues. In particular, the present invention relates to techniques for noninvasively determining FRC or ELV.

2. Background of Related Art

Functional residual capacity (FRC) is the volume of gases, including carbon dioxide ($CO_2$), that remains within the lungs of a subject at the end of exhalation, or expiration. In healthy individuals, FRC usually comprises about 40% of total lung capacity, and typically amounts to about 1.8 liters to about 3.4 liters. FRC buffers against large breath-to-breath changes in the amount of carbon dioxide in the alveoli of the subject's lungs, which may be measured in terms of partial pressure of $CO_2$ ($p_{ACO2}$) or as a fraction of gases that comprise $CO_2$ ($f_{ACO2}$). With normal tidal volumes, $p_{ACO2}$ and $f_{ACO2}$ typically fluctuate by only about 2 mmHg or about 0.25%, respectively.

A number of authors contend that $CO_2$ is stored in the lungs in three different compartments: (1) the gas volume ($V_A$ or FRC); (2) the lung tissue; and (3) the pulmonary blood present at any given time in the lung. The lung tissue and pulmonary blood compartments are often represented in terms of their equivalent gas volumes (i.e., scaled by their effective storage capacity) and denoted $V_{tis}$ and $V_{blood}$. While FRC only accounts for the volume of gases (including $CO_2$) in the alveoli, effective lung volume (ELV) includes FRC, as well as gases that remain diffused within the tissues of the lungs of the subject at the end of exhalation and, therefore, accounts for gases in all three compartments.

While ELV is typically a slightly larger volume than FRC, these terms may be used interchangeably in the ensuing description for purposes of simplicity.

Each compartment equilibrates with changes in $CO_2$ at a different rate. Gedeon, A., et al., "Pulmonary blood flow (cardiac output) and the effective lung volume determined from a short breath hold using the differential Fick method," J. Clin. Monit. 17:313-321 (2002) (hereinafter "Gedeon 2002") teaches that $V_A$ equilibrates instantly with changes in end tidal $CO_2$ ($p_{etCO2}$ when measured in terms of partial pressure and $f_{etCO2}$ when measured in terms of the fraction of gases that comprise $CO_2$) and slowly (e.g., in about ten to about twenty seconds) with changes in $p_{ACO2}$ and content of $CO_2$ in arterial blood ($c_{aCO2}$), while it takes less time for $V_{tis}$ and $V_{blood}$ to equilibrate when $p_{ACO2}$ and $c_{aCO2}$ change.

The relationship between a subject's chest wall and lungs and the elastic recoil of the lungs defines FRC and, thus, ELV. Lung diseases that change the elastic recoil of the lungs, including emphysema, asthma, and other restrictive diseases, affect FRC. Thus, FRC determinations may be useful in accurately diagnosing such conditions. FRC determinations are also useful in diagnosing and treating respiratory failure and hypoxemia.

In lungs with an FRC below the lung's closing capacity, the airways start to close before the end of a subject's exhalation, which results in a decrease of $p_{AO2}$ and a mismatch between ventilation, or the movement of gases into and out of the lungs through the mouth, and perfusion, or the movement of gases across the gas/blood barrier between the alveoli of the lungs and the pulmonary capillaries that surround the alveoli. This is known in the art as V/Q mismatch or $V_T/V_Q$ mismatch.

The currently available techniques for measuring FRC include full body plethysmography, nitrogen washout, and helium dilution. All of these methods require cumbersome equipment and, therefore, may not be suitable for use in an intensive care setting that is already crowded with equipment.

Gedeon 2002 proposed a noninvasive technique for determining ELV. Specifically, that technique includes measuring the $\dot{V}_MCO_2$ and $f_{etCO2}$ of a subject, having the subject hold his or her breath for three seconds, the re-measuring $\dot{V}_MCO_2$ and $f_{etCO2}$. For the first breath following the breath-hold, $f_{etCO2}$ increases and $\dot{V}_MCO_2$, which is calculated over the duration of the breath hold and the subsequent breath, decreases. Assuming, due to buffering by the $CO_2$ stores of the ELV, that $\dot{V}_BCO_2$ (i.e., $CO_2$ passing from the pulmonary capillary blood into the alveoli of the lung) does not change during breath-holding, Gedeon contends that the decrease in $\dot{V}_MCO_2$ must have resulted from the $CO_2$ going into the lung stores of $CO_2$:

$$[f_{etCO2\ POST}-f_{etCO2\ PRE}]\times \hat{V}_A{}^* = [\dot{V}_MCO_{2PRE}-\dot{V}_MCO_{2POST}]\times [T_{breath}+T_{breathhold}]$$

where $[\dot{V}_MCO_{2PRE}$ and $\dot{V}_MCO_{2POST}$ refer to measurements obtained respectively before and after the breath-holding maneuver.

In addition to this relationship, Gedeon developed equations that relate pulmonary capillary blood flow (PCBF or, for the sake of simplicity in the ensuing equations, $\dot{Q}$) of the subject to the subject's ELV. Two of these equations compare the pre-breathhold conditions to the post-breathhold conditions and the pre-breathhold conditions to the recovery conditions. The ELV of an ELV and PCBF data pair that satisfies both of these equations is considered to be the subject's actual ELV.

The technique of Gedeon 2002 is believed to provide inaccurate data, as it is based on the assumption that "$CO_2$ inflow [may] not [be] significantly affected" by breath-holding, while breath-holding will cause a change in $p_{ACO2}$. This assumption is inconsistent with the Fick equation, in which $\dot{V}_BCO_2$ changes linearly with $p_{ACO2}$ while PCBF and the amount of $CO_2$ in the venous blood ($c_{vCO2}$ or, as Gedeon2002 refers to it, $p_{ven}$) remain constant.

In view of the foregoing, it is apparent that there is a need for a technique for accurately, noninvasively measuring FRC or ELV in virtually any healthcare setting.

SUMMARY OF THE INVENTION

The present invention includes methods for noninvasively measuring, or estimating, FRC or ELV, as well as apparatus and systems for obtaining FRC and ELV measurements with minimal invasiveness.

As an example of a method for noninvasively measuring, or estimating, FRC or ELV in accordance with teachings of the present invention, carbon dioxide and flow measurements may be obtained at or near the mouth of a subject. Such measurements are obtained during baseline, or "normal,"

breathing, as well as during and shortly after inducement of a change in the subject's effective ventilation. For example, measurements may be obtained during or shortly following a rebreathing maneuver, in which a subject inhales gases including an above-normal amount of $CO_2$. Continuing with the rebreathing example, the obtained measurements are evaluated to determine the amount of time required for exhaled $CO_2$ levels to return to normal—effectively an evaluation of $CO_2$ "washout" from the subject's lungs. Conversely, $CO_2$ and flow measurements may be evaluated to determine the amount of time it takes $CO_2$ to "wash in," or reach peak levels within, the lungs of the subject following rebreathing. Of course, when other techniques are used to generate a perturbation, or change, in the effective ventilation (i.e., the total ventilation less the wasted ventilation due to deadspace associated with the apparatus, the individual, or a combination thereof) of a subject, amounts of $CO_2$ or another appropriate gas may be measured. By evaluating such measurements, the ELV of the subject may be substantially noninvasively determined, or estimated.

A noninvasive ELV estimation apparatus that incorporates teachings of the present invention is configured (e.g., programmed) to evaluate $CO_2$ and flow data from a subject and process the same in such a way as to calculate ELV. A system of the present invention includes such an apparatus, as well as $CO_2$ and flow sensors, which obtain $CO_2$ and flow measurements in as noninvasive a manner as possible (with the possible exception of an endotracheal tube) and communicate data representative of the measured $CO_2$ and flow levels to the noninvasive ELV estimation apparatus.

Other features and advantages of the present invention will become apparent to those of ordinary skill in the art through consideration of the ensuing description, the accompanying figures, and the appended claims.

BRIEF DESCRIPTION OF THE FIGURES

In the figures, which illustrate various exemplary aspects of the present invention.

DETAILED DESCRIPTION

Figure 1:
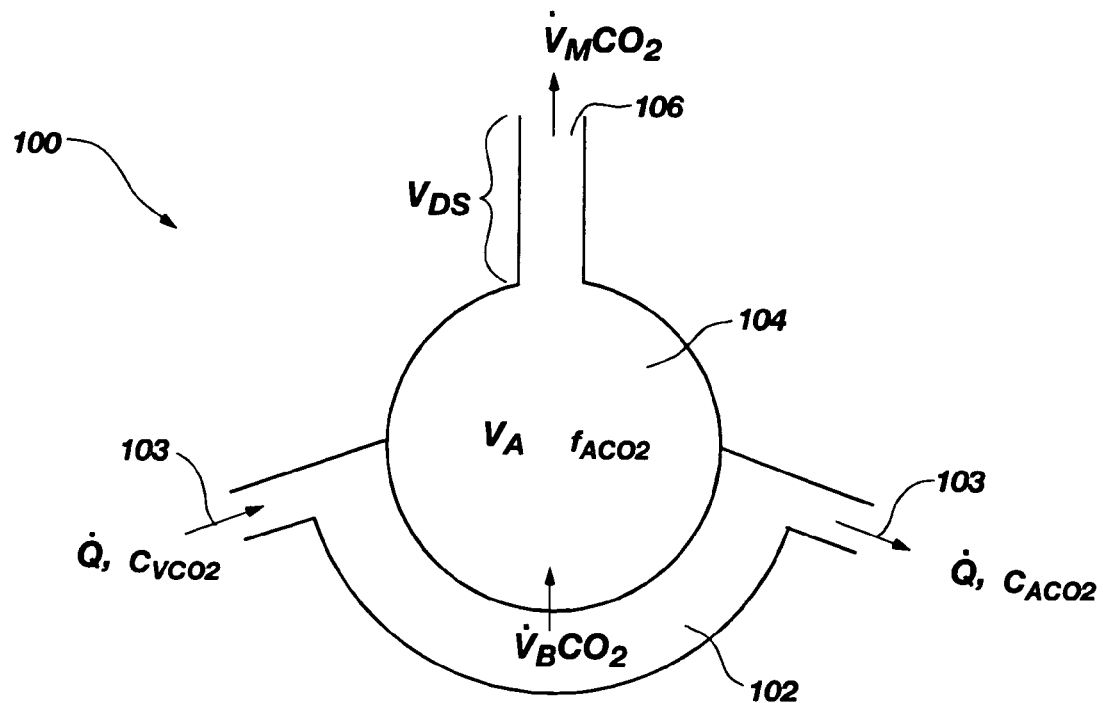
FIG. 1 is a schematic representation of an alveolus of an individual, illustrating the locations at which various respiratory and blood gas parameters may be determined.

The present invention includes methods for determining the FRC or ELV of a subject substantially noninvasively. In the inventive methods, FRC or ELV may be determined by evaluating a respiratory gas, such as carbon dioxide, and respiratory flow. Respiratory gas and flow signals may be used to determine a variety of parameters and, along with a mathematical model of the subject's lung, used to determine FRC or ELV. The ensuing description includes a discussion of the manner in which one or more exemplary algorithms are derived, as well as reasoning to support such derivation, to facilitate substantially a noninvasive determination of the subject's FRC or ELV.

In accordance with teachings of the present invention, FRC and ELV may be determined while the respiratory and cardiovascular, or hemodynamic, performance of a subject is being determined in a substantially noninvasive manner. Exemplary measures of the cardiovascular performance of a subject include, but are not limited to, pulmonary capillary blood flow and cardiac output.

The carbon dioxide Fick equation has long been used to determine both pulmonary capillary blood flow and cardiac output. One form of the carbon dioxide Fick equation follows:

$$PCBF = VCO_2 / (c_{vCO2} - c_{ACO2}), \tag{1}$$

where PCBF represents pulmonary capillary blood flow, $VCO_2$ is carbon dioxide elimination, $c_{vCO2}$ is carbon dioxide content of the venous blood of the monitored individual, and $c_{ACO2}$ is the carbon dioxide content of the alveolar (i.e., pulmonary capillary) blood of the monitored individual.

The most accurate way to measure $VCO_2$ would be to directly measure the flow of $CO_2$ from the blood within the pulmonary capillaries that surround the alveoli of the lungs to the alveoli, or carbon dioxide excretion ($\dot{V}_B CO_2$). If $VCO_2$ could be measured in this manner, equation (1) becomes:

$$PCBF = \frac{\dot{V}_B CO_2}{c_{vCO2} - c_{ACO2}} \tag{2}$$

If the content of $CO_2$ in blood at the alveolus ($c_{ACO2}$) is substantially the same as the content of $CO_2$ in arterial blood ($c_{aCO2}$), then cardiac output ($\dot{Q}$) may be substituted for PCBF in equation (2).

Rearranging equation (2) for a calculation of $\dot{V}_B CO_2$ results in the following:

$$\dot{V}_B CO_2 = -PCBF \, c_{ACO2} + PCBF \, c_{vCO2}. \tag{3}$$

Notably, equation (3) takes the form of the standard equation for a line in a two-dimensional (x, y) coordinate system: y=mx+b. When $\dot{V}_B CO_2$ signals (y-axis) are plotted in a two-dimensional coordinate system against $c_{ACO2}$ signals (α-axis) taken at various points during and before or after a change in the effective ventilation of an individual, it can be seen the slope (m) of a line extending through the plotted points will be −PCBF, while PCBF $c_{vCO2}$ is the intercept (b).

Equations (2) and (3) are based on the rate at which carbon dioxide leaves, or is eliminated from, the blood at the alveoli ($\dot{V}_B CO_2$). If the flow of $CO_2$ from the blood into the alveoli, or carbon dioxide excretion ($\dot{V}_B CO_2$), could be measured and plotted against $c_{ACO2}$ during rebreathing or another change in the effective ventilation of the subject, data from every breath, including transitional data points, would fall on the line defined by equation (3).

Unfortunately, $\dot{V} CO_2$ is not measured directly at the alveoli. It is measured in a less direct manner—at or near the subject's mouth. Carbon dioxide signals that originate at or near the mouth of a subject are typically obtained and processed, along with respiratory flow signals, to facilitate such measurements. Notably, U.S. Patent Publication U.S. 2002/0183643 A1 of Kück et al. (hereinafter "Kück"), the disclosure of which is hereby incorporated herein, in its entirety, by this reference, teaches that measurements of $CO_2$ that are taken at the mouth of a subject as the subject exhales do not necessarily correlate well with the amount of $CO_2$ that is given off by the blood as it passes by the alveoli of the subject's lungs. More specifically, $CO_2$ that is exhaled, or eliminated, from the subject's respiratory system, as measured at or near the subject's mouth ($\dot{V}_M CO_2$) ultimately results from but does not correlate well with the amount of $CO_2$ that is excreted from the blood to the lungs of the subject ($\hat{\dot{V}}_B CO_2$, when considered in terms of flow) during the same breath. Kück explains that such miscorrelation is caused by the $CO_2$ stores of a subject's lungs, specifically by the buffering capacity of the $CO_2$ stores.

More specifically, $\dot{V}_M CO_2$ includes both $\dot{V}_B CO_2$ and $CO_2$ that has flowed into or out of the ELV of the subject's lungs, which include $CO_2$ stores ($\dot{V}_{STORES} CO_2$). Thus, $$\dot{V}_B CO_2 = \dot{V}_M CO_2 - \dot{V}_{STORES} CO_2. \quad (4)$$

The $CO_2$ stores of a subject's lungs act as a buffer, absorbing some of the increased $CO_2$ and causing $\dot{V}_M CO_2$ to change more gradually than $\dot{V}_B CO_2$ changes.

The $CO_2$ stores of an individual's lungs may be evaluated by use of a model of the lung, such as the simple model of the lung depicted in FIG. 1, in which a single alveolus 100 and a corresponding pulmonary capillary 102 represent the lung. The direction in which blood flows through pulmonary capillary 102 is represented by arrows 103. The mouth of an individual is represented at reference 106. In the model of FIG. 1, the carbon dioxide stores of the lung are depicted, for the purpose of simplicity, as comprising the physical gas volume 104 of the alveolus ($V_A$). As is known in the art, $V_A$ is related to tidal volume ($V_T$), as well as to the functional residual capacity ($V_{FRC}$) of the lung. In addition to the illustrated contributors to the $CO_2$ stores of the lung (i.e., FRC), $CO_2$ may be distributed within other stores, such as the alveolar tissues and other tissues of the lung (collectively the ELV). The lung model shown in FIG. 1 also omits $V_T/V_Q$ mismatch and shunting of blood (i.e., the portion of cardiac output that does not flow through the pulmonary arteries and capillaries, or that is not PCBF). For modeling purposes, the mixing of air within the alveolus (including inspired gases, $CO_2$ escaping from the blood, flow of $CO_2$ into and out of the $CO_2$ stores, and gases within the alveolus) is assumed to occur instantaneously. The effective volume of the $CO_2$ stores of an individual's lungs are denoted herein as "$V_A^*$."

Figure 2:
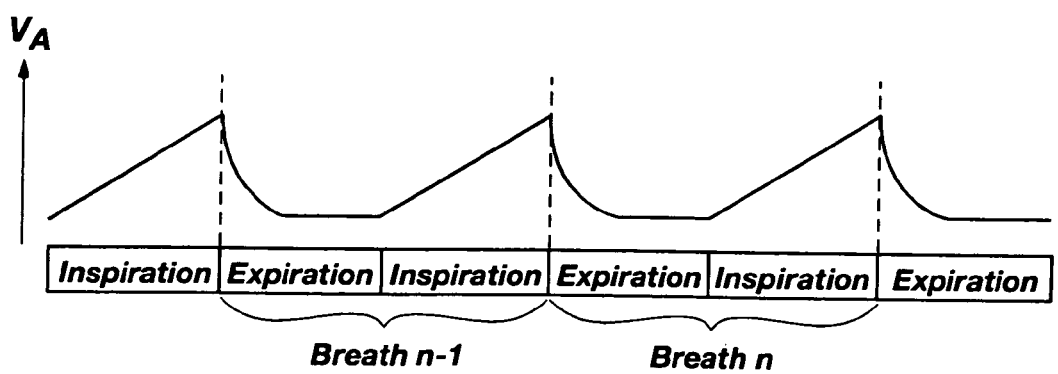
FIG. 2 is a graph that illustrates the volume of gases in the carbon dioxide stores of a respiratory tract of an individual ($V_A$) during a series of respiratory cycles, or breaths.

The effects of the $CO_2$ stores may be evaluated to obtain an accurate $\dot{V}_B CO_2$ based on direct $\dot{V}_M CO_2$ measurements. For example, a model of the lung, such as that depicted in FIG. 1, may be evaluated on a breath-by-breath basis. By way of example only, a breath (n) may be delineated as the period from the end of one inspiration to the end of the next inspiration, as illustrated in FIG. 2. In addition, FIG. 2 depicts an example of the effective volume of $CO_2$ stores in the subject's respiratory tract (e.g., lungs) during the course of respiration.

If the effective volume of $CO_2$ stores ($V_A^*$) does not change from breath to breath, the amount of $CO_2$ that flows into and out of the $CO_2$ stores from one breath to the next may be expressed as a change in alveolar $CO_2$ fraction ($f_A CO_2$) (i.e., the fraction of gases in the alveolus that comprise $CO_2$), or the difference between $f_A CO_2$ for a particular breath ($f_A CO_2(n)$) and $f_A CO_2$ for the previous breath $f_A CO_2(n-1)$. Thus, the volume of the $CO_2$ stores ($V_{STORES} CO_2$) for a particular breath (n) may be determined by multiplying the effective volume in which the $CO_2$ stores are located ($V_A^*$) by the change in $f_A CO_2$ from the previous breath (n-1) to the current breath (n) and by the subject's respiratory rate (RR). Equation (4) then becomes:

$$\dot{V}_B CO_2(n) = \dot{V}_M CO_2(n) + V_A^*(n)[f_A CO_2(n) - f_A CO_2(n-1)]RR. \quad (5)$$

Equation (5) is particularly useful for estimating $\dot{V}_B CO_2$ from $\dot{V}_M CO_2$ measurements that are obtained during the transition from "normal" breathing (e.g., nonrebreathing) to a change in the effective ventilation of the subject (e.g., rebreathing or another change in the effective ventilation). An estimate of $\dot{V}_B CO_2$ is denoted herein as $\hat{\dot{V}}_B CO_2$ and may be substituted for $\dot{V}_B CO_2$ in equation (5).

While $\dot{V}_M CO_2$ and RR may be measured directly, the alveolar $CO_2$ fraction ($f_{ACO2}$) and $V_A^*$ cannot. It is known, however, that $f_{ACO2}$ is proportional to $p_{ACO2}$, which is proportional to $p_{etCO2}$, which may be measured directly (e.g., by use of a capnometer). The $p_{etCO2}$ measurement may then be used, as known in the art, to obtain an $f_{ACO2}$ value for each breath.

Figure 3:
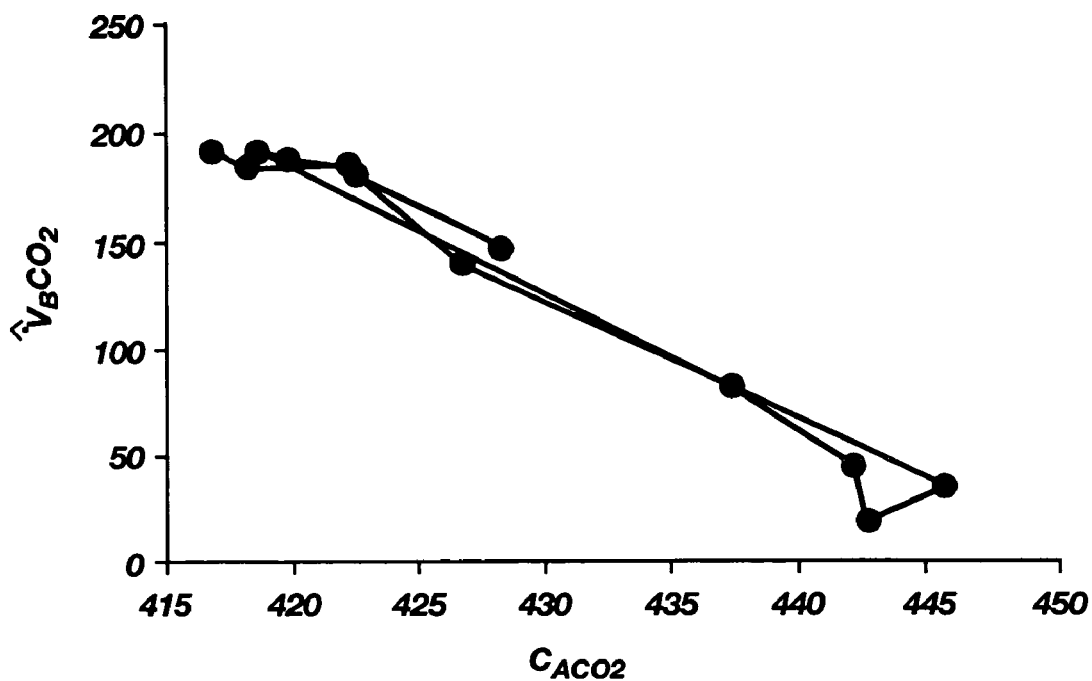
FIG. 3 is a plot of the transformed $\hat{V}_M CO_2$ data points against $c_{ACO2}$ data points, in which the plotted points are substantially in-line with one another.

$V_A^*$ may be adaptively estimated, such as by using the linear correlation between $\hat{\dot{V}}_B CO_2$ from equation (5), substituting $\hat{V}_A^*$, the estimated effective alveolus volume, for $V_A^*$, the actual effective alveolus volume, and using $c_{ACO2}$ as a guide (see equation (3)). The more accurately $\hat{V}_A^*$ reflects $V_A^*$, the closer the data points of a plot of $\hat{\dot{V}}_B CO_2$ against $c_{ACO2}$ (which is also proportional to and may be determined from $p_{etCO2}$ measurements in a manner known in the art) over the course of a change in the effective ventilation of an individual will be to a line representative of the actual pulmonary capillary blood flow or cardiac output of the individual. The ideal value for $\hat{V}_A^*$ may, therefore, be determined as the value that results in the best linear fit between the plotted data ($c_{ACO2}$ against $\hat{\dot{V}}_B CO_2$) and, thus, a maximized correlation coefficient, or $r^2$ value. By way of example only, an adaptive, iterative, or search algorithm of a type known in the art may be used to determine $\hat{V}_A^*$ for which the correlation coefficient, or $r^2$, is maximized. The graph of FIG. 3 shows an example of a $\hat{V}_A^*$ value at which $r^2$ is maximized.

Once an accurate $\hat{V}_A^*$ estimate has been made, the effective volume of the FRC ($V_{FRC}$) or ELV ($V_{ELV}$) of the subject's lungs may also be estimated or determined. In this regard, equation (5) may be rewritten, as follows, to reflect the use of $\hat{V}_A^*$ as an estimate for $V_A^*$:

$$\hat{\dot{V}}_B CO_2(n) = \dot{V}_M CO_2(n) + \hat{V}_A^*(n)[f_{ACO2}(n) - f_{ACO2}(n-1)]RR. \quad (6)$$

The foregoing approach (particularly, the use of equation (6)) works well when a subject is mechanically ventilated (i.e., on a respirator), in which case the respiratory rate and tidal volume ($V_T$) of the individual's respiration are typically substantially stable, which provides for a "clean" $f_{ACO2}$ signal.

During spontaneous or mixed (i.e., mechanical and spontaneous) ventilation, it may be desirable to eliminate any noise that may occur in the $f_{ACO2}$ signal when equation (6) is used, as such noise may result in an inaccurate estimation of $\dot{V}_B CO_2$ (i.e., $\hat{\dot{V}}_B CO_2$). An algorithm that is less sensitive to noise than equation (6) may, therefore, also be useful for estimating $\hat{\dot{V}}_B CO_2$, as described hereinafter.

Assuming that pulmonary capillary blood flow and cardiac output do not change from one breath to the next, the carbon dioxide Fick equation (equation (2)) may be rewritten for two successive breaths:

$$PCBF = \frac{\dot{V}_B CO_2(n-1)}{c_{vCO2}(n-1) - c_{ACO2}(n-1)} = \frac{\dot{V}_B CO_2(n)}{c_{vCO2}(n) - c_{ACO2}(n)} \quad (7)$$

Further, assuming that $c_{vCO2}$ does not change from one breath to the next, equation (7) may be simplified to:

$$PCBF = \frac{\dot{V}_B CO_2(n-1) - \dot{V}_B CO_2(n)}{c_{ACO2}(n) - c_{ACO2}(n-1)} \tag{8}$$

Measurements of the $CO_2$ fraction of gases in a subject's alveoli ($f_{ACO2}$) may be used in place of the $c_{ACO2}$ measurements of equation (8) when the slope of the $CO_2$ dissociation curve ($s_{CO2}$), a standard curve which illustrates the rate at which $CO_2$ molecules dissociate from the hemoglobin molecules of red blood cells, and barometric pressure ($p_{baro}$) are also taken into consideration, as known in the art. Accordingly, equation (8) may be rewritten as follows:

$$PCBF = \frac{\dot{V}_B CO_2(n-1) - \dot{V}_B CO_2(n)}{s_{CO2}\, p_{baro}\, f_{ACO2}(n) - f_{ACO2}(n-1)} \tag{9}$$

Solving this expression for the difference in $CO_2$ fractions ($f_{ACO2}(n) - f_{ACO2}(n-1)$) yields:

$$f_{ACO2}(n) - f_{ACO2}(n-1) = \frac{\dot{V}_B CO_2(n-1) - \dot{V}_B CO_2(n)}{s_{CO2}\, p_{baro}\, PCBF} \tag{10}$$

Substitution of equation (10) into equation (6) results in:

$$\hat{\dot{V}}_B CO_2(n) = \dot{V}_M CO_2(n) + \tag{11}$$

$$\frac{RR\, \hat{V}_A*(n)}{s_{CO2}\, p_{baro}\, PCBF} [\hat{\dot{V}}_B CO_2(n-1) - \hat{\dot{V}}_B CO_2(n)]$$

This expression can now be solved for $\hat{\dot{V}}_B CO_2(n)$ to provide an accurate estimate of $\dot{V}_B CO_2$:

$$\hat{\dot{V}}_B CO_2(n) = \frac{1}{1 + \frac{RR\, \hat{V}_A*(n)}{s_{CO2}\, p_{baro}\, PCBF}} \dot{V}_M CO_2(n) + \tag{12}$$

$$\frac{\frac{RR\, \hat{V}_A*(n)}{s_{CO2}\, p_{baro}\, PCBF}}{1 + \frac{RR\, V_A*(n)}{s_{CO2}\, p_{baro}\, PCBF}} \hat{\dot{V}}_B CO_2(n-1)$$

Structurally, this result represents a first order, single-pole low pass filter of the form $$\hat{\dot{V}}_B CO_2(n) = (1-\alpha)\dot{V}_M CO_2(n) + \alpha \hat{\dot{V}}_B CO_2(n-1), \tag{13}$$

where $\alpha$, the transformation coefficient, may be represented as $$\frac{\frac{RR\, \hat{V}_A*(n)}{s_{CO2}\, p_{baro}\, PCBF}}{1 + \frac{RR\, V_A*(n)}{s_{CO2}\, p_{baro}\, PCBF}}. \tag{14}$$

The RR in equation (14), which is the respiratory rate of the subject, is measured in breaths per minute. $\hat{V}_A*(n)$ is estimate of the $CO_2$ stores of the subject's lungs during breath (n) and is approximately equivalent to the volume of the FRC or ELV of the subject's lungs ($V_{FRC}*$ and $V_{ELV}*$, respectively). $s_{CO2}$ is the slope of the standard carbon dioxide dissociation curve. $p_{baro}$ is barometric pressure. PCBF, the pulmonary capillary blood flow the subject, does not need to be known to determine either $\alpha$ or $\hat{V}_A*(n)$.

It is not necessary to know PCBF to calculate $\alpha$ because a determination of $\alpha$ merely requires that the linearity, or straightness, of a line through $\dot{V}_B CO_2$ values that have been plotted against $p_{etCO2}$ or $c_{CO2}$ values be evaluated, not that the slope of the line, which is equal to PCBF, be evaluated. In that regard, the transformation coefficient ($\alpha$) in equations (13) and (14) may be determined iteratively, by using an initial $\alpha$ value, then progressively increasing and/or decreasing the $\alpha$ value to determine the $\alpha$ value that provides for a plot of $\dot{V}_B CO_2$ values against $p_{etCO2}$ or $c_{CO2}$ values with the greatest linearity (as opposed to an open loop) or, stated another way, that provides an optimal correlation coefficient ($r^2$) between the $\dot{V}_B CO_2$ values and the $p_{etCO2}$ or $c_{CO2}$ values. Other methods for determining an optimal $\alpha$ value include, without limitation, rote searching, global searching, gradient searching (e.g., use of a gradient descent search algorithm), use of a least mean squares algorithm, use of other predetermined equations or sets of predetermined equations, use of a truly adaptive filtering technique, and use of other techniques to determine the optimal $\alpha$ value, as known in the art.

Use of an optimal transformation coefficient ($\alpha$) (equation (14)) in equation (13) provides a relatively accurate, simple mathematical model of the lung of a subject. The algorithm of equation (13) may be used to calculate the amount of $CO_2$ that flows into and out of the carbon dioxide stores of the lungs on a "breath-to-breath" basis.

The $\hat{V}_A*(n)$ of equation (14) is equivalent to ELV and flow may be converted to volume, which results in elimination of RR, allowing $\alpha$ to be expressed more simply as:

$$\alpha = \frac{\hat{V}_A*}{s_{CO2}\, p_{baro}\, PCBF/RR + \hat{V}_A*}, \tag{15}$$

where Q is measured in terms of volume, rather than flow. If equation (15) were multiplied through with $\Delta f_{ACO2}$ (i.e., $f_{ACO2}(n) - f_{ACO2}(n-1)$, the expression could be viewed as calculating the relative amount of $CO_2$ stored in ELV over the total change in the amount of $CO_2$ from a change in the effective ventilation of a subject (e.g., rebreathing or another change in effective ventilation).

If PCBF/RR is calculated from data obtained before and during a change in the effective ventilation of the subject (e.g., rebreathing or another change in effective ventilation), equation (15) may be rewritten as follows:

$$\alpha = \frac{\hat{V}_A^*}{\frac{\Delta V CO_2}{\Delta f_{CO2}} + \hat{V}_A^*} \quad (16)$$

Equation (16) may be rearranged as follows:

$$\hat{V}_A^* = \frac{\alpha}{1-\alpha}(PCBF/RR)s_{CO2}p_{Baro} \quad (17)$$

to solve for ELV ($\hat{V}_A^*$)

Equation (17) may be used to substantially noninvasively determine ELV when virtually any change in the effective ventilation of the subject (e.g., rebreathing, change in respiratory rate, change in respiratory volume, etc.) has occurred, whether or not the subject continues to breathe as data is collected, with data obtained during "normal" breathing being compared with data obtained once the change in effective ventilation has occurred.

Other techniques for determining an optimal α value are also within the scope of the present invention.

Equation (6) does not take into account the possibility, or even likelihood, that the amount of $CO_2$ stored within the lungs ($\dot{V}_{STORES}CO_2$) may vary from breath to breath. A more complex version of equation (6) accounts for this possibility:

$$\dot{V}_B CO_2(n) = \dot{V}_M CO_2(n) + (\hat{V}_A^*(n) + V_T(n)) \times (f_{ACO2}(n) - f_{ACO2}(n-1)) + (V_T(n) - V_T(n-1)) \times f_{ACO2}(n), \quad (18)$$

Accordingly, in another aspect, the present invention includes use of an algorithm that corrects ELV for possible changes in $V_{CO2STORES}$ and combines the ELV correction with the $CO_2$ form of the differential Fick equation:

$$\dot{Q} = \frac{\overline{V}_M CO_2 - (\dot{V}_M CO_2(n) + \hat{V}_A^* \cdot [f_{ACO2}(n) - f_{ACO2}(n-1)])}{s_{CO2} \cdot (p_{ACO2}(n) - \overline{p}_{ACO2})} \times RR, \quad (19)$$

where $\overline{\nabla}_M CO_2$ is the average breath-to-breath volume, not flow, of carbon dioxide eliminated from the subject's lungs, as measured at the mouth, during breaths that precede and effective change in the ventilation of the subject (e.g., rebreathing or another change in effective ventilation). The ELV value of equation (19) includes tidal volume ($V_T$). For a closer estimate of FRC, the inspiratory tidal volume should be subtracted from ELV, as estimated for use in equation (19). Notably, accurate results may be obtained when $\dot{V}_M CO_2$ (n) for each breath is calculated from expiration to inspiration (i.e., as $\dot{V}_M CO_2$ (n)=$\dot{V}_M CO_2$ $_{expired}$(n−1)−$\dot{V}_M CO_2$ $_{inspired}$(n)).

Tidal volumes typically do not change drastically from breath-to-breath. Therefore, the expression $V_T(n) - V_T(n-1)$ from equation (18) has been omitted from equation (19) without substantially affecting the accuracy of a subsequent ELV determination. Optionally however, a variation of equation (19) may consider the change in tidal volume from one breath to the next, as doing so could improve the accuracy of the $\dot{Q}$ calculation and, thus, of the subsequent ELV estimation.

If $\dot{V}_M CO_2$ and $p_{etCO2}$ reach good plateaus within a cycle, it might be possible to use them to calculate PCBF in equation (19). This is possible because ELV does not affect PCBF estimations from plateau values (algebraically, the $f_{ACO2}(n) - f_{ACO2}$ (n−1) term vanishes at plateaus).

Equation (19) can be solved for ELV ($\hat{V}_A^*$):

$$\hat{V}_A^* = \frac{1}{f_{ACO2}(n) - f_{ACO2}(n-1)} \cdot \Big[ V_M CO_{2PRE} - V_M CO_2(n) - PCBF \cdot s_{CO2} \cdot (p_{ACO2}(n) - p_{ACO2 PRE}) \cdot \frac{1}{RR} \Big] \quad (20)$$

Furthermore, if it is assumed that one $CO_2$ dissociation curve slope $s_{CO2}$ (e.g., the average across the cycle's $p_{etCO2}$ values) can be used, then it cancels and the equation simplifies to:

$$\hat{V}_A^* = \frac{1}{f_{ACO2}(n) - f_{ACO2}(n-1)} \cdot \Big[ V_M CO_{2PRE} - V_M CO_2(n) - \frac{V_M CO_{2PRE} - V_M CO_{2DUR}}{p_{ACO2DUR} - p_{ACO2 PRE}} \cdot (p_{ACO2}(n) - p_{ACO2 PRE}) \Big] \quad (21)$$

where the pre and during values represent the respective plateaus. Alternatively, PCBF can be determined through some other method, be it invasive (e.g., thermodilution), or noninvasive (e.g., electrical bioimpedance).

Parts of equation (21) may be used in at least two embodiments of the present invention, one of which includes use of the first part of equation (21) to determine ELV. More specifically, if one could assume that $\dot{V}_B CO_2$ is constant even though the $p_{ACO2}$ is changing due to a change in the effective ventilation of the subject (e.g., rebreathing or another change in effective ventilation), ELV may be determined as follows:

$$\hat{V}_A^* = \frac{1}{f_{ACO2}(n) - f_{ACO2}(n-1)} \cdot [V_M CO_{2PRE} - V_M CO_2(n)] \quad (22)$$

Equation (22) may be used to evaluate ELV when a change in the effective ventilation of the subject (e.g., rebreathing, change in respiratory rate, change in respiratory volume, etc.) has been effected, and while the subject continues to breathe (i.e., not during maneuvers which require breath-holding or which otherwise temporarily terminate breathing). In using equation (22) to determine ELV, data obtained during "normal" breathing may be compared with data obtained once the change in effective ventilation has occurred. For example, and not by way of limitation, breath (n−1) may represent a normal breath, while (n) may represent the first breath in which the change in effective ventilation has occurred.

The second of these embodiments employs both the first part of equation (21) (i.e., equation (22), as well as the second part of equation (21):

$$- \frac{VCO_{2PRE} - VCO_{2DUR}}{p_{ACO2DUR} - p_{ACO2 PRE}} \cdot (p_{ACO2}(n) - p_{ACO2 PRE}) \Big] \quad (23)$$

or a broader variation thereof:

$$PCBF \cdot s_{CO2} \cdot \frac{1}{RR} \cdot (p_{ACO2}(n) - p_{ACO2 PRE}) \quad (24)$$

In this manner, the ELV calculation of equation (22) may be modified to compensate for changes in $p_{ACO2}$ during a breath, or continuously changing $p_{ACO2}$. Specifically, the ratio of the change in $VCO_2$ to the change in $p_{ACO2}$ in equation (23) and of $\dot{Q}$ in equation (24) represents the slope of the line that describes the amount of $CO_2$ that exits the $CO_2$ stores through the mouth as $CO_2$ exiting the blood is added to the $CO_2$ stores, or the "sensitivity" with which changes in $p_{etCO2}$ represent changes in $p_{ACO2}$ as $CO_2$ from the blood flows into the $CO_2$ stores, which in turn provides an indication of buffering capacity of the $CO_2$ stores. $(p_{ACO2}(n)-\overline{p}_{ACO2})$ provides an indication of the magnitude of the $p_{ACO2}$ change to be scaled when $p_{etCO2}$ is measured at or near the mouth.

The $$\frac{1}{RR}$$

in equation (24) may be substituted with a different value that represents the time interval between the start of a change in effective ventilation (e.g., rebreathing) and the time when the measured $p_{ACO2}$ left the alveoli. Generally, such a value will be less than $$\frac{1}{RR}.$$

The combination of equations (23) and (24) may be used to substantially noninvasively determine ELV when virtually any change in the effective ventilation of the subject has occurred, whether or not the subject continues to breathe as data is collected. More specifically, data obtained during "normal" breathing may be compared with data obtained once the change in effective ventilation has occurred.

Figure 4:
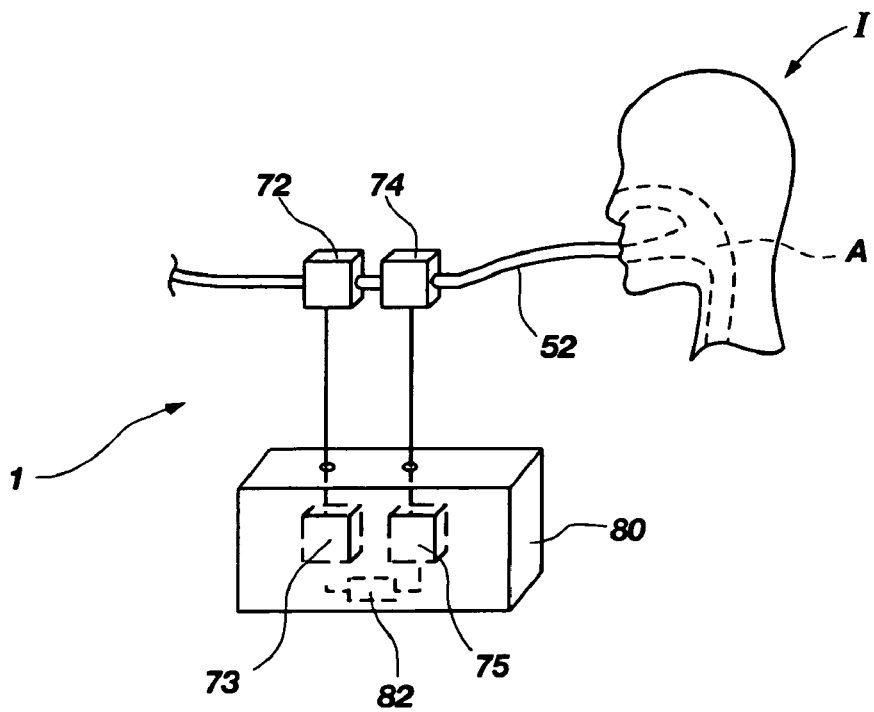
FIG. 4 is a schematic representation of an example of a monitoring system incorporating teachings of the present invention.

Turning now to FIG. 4, an exemplary diagnostic system 1 that incorporates teachings of the present invention is schematically illustrated. Diagnostic system 1 includes, among other things, an airway 52 in communication with the airway A of an individual I, as well as a flow meter 72 and a carbon dioxide sensor 74 positioned along airway 52. Flow meter 72 and carbon dioxide sensor 74 communicate signals to corresponding monitors 73 and 75, which communicate electronically with a processor 82 of a respiratory monitor 80 (e.g., the processor and respiratory monitor of a NICO® monitor available from Novametrix Medical Systems (Wallingford, Conn.) division of Respironics, Inc). Processor 82 is programmed to determine at least $VCO_2$ and $p_{etCO2}$ based on signals communicated thereto from flow meter 72 and carbon dioxide sensor 74. In addition, processor 82 may be programmed to use signals from one or both of flow meter 72 and carbon dioxide sensor 74 or calculated parameters (e.g., $VCO_2$ and $p_{etCO2}$) in the above-described algorithms (i.e., one or more of equations (1)-(24)) to facilitate the substantially noninvasive and accurate determination of individual I's ELV. Alternatively, such calculations may be made manually.

In a method that incorporates teachings of the present invention, $VCO_2$ and $p_{etCO2}$ values are obtained during both a baseline, or first, ventilatory state, and when a change in the effective ventilation of individual I has been effected, or a second ventilatory state. Alternatively, such values may obtained during a transition between first and second states, then compared with values obtained during the first or second state.

The first ventilatory state may be effected under substantially "normal" breathing conditions. Alternatively, the baseline ventilatory state may be defined under a first set of other, selected breathing conditions. The second ventilatory state occurs when one or more respiratory control parameters are manipulated to achieve breathing conditions differ from those present during the first ventilatory state to a degree that effect a measurable change in minute ventilation.

The second ventilatory state may be induced, for example, by altering the value of a limit variable, e.g., inspiratory pressure, tidal volume, flow rate or time, from a value of the limit variable during the first ventilatory state. In another exemplary method, a change in effective ventilation may be induced by altering the threshold value of a cycle variable from the threshold level of the cycle variable during the first ventilatory state. In a further exemplary method, a change in effective ventilation may be induced by altering the threshold triggering value of a triggering variable, such as inspiratory pressure or flow rate. In a still further method, a change in effective ventilation may be induced by delivering to the individual a series of at least three "sigh breaths," which are deeper than normal breaths. Changes in effective ventilation may also comprise periods of unsteady, or "noisy," breathing.

The $VCO_2$ and $p_{etCO2}$ values that are obtained are then processed in accordance with one or more of equations (1)-(24)) to substantially noninvasively and accurately determine individual I's ELV.

EXAMPLE

Different effective FRC values were achieved by incrementally advancing an especially long endotracheal tube from an initial, normal position to a small distance within the bronchial tree of an anesthetized pig (at time=15:26) and, twenty-one minutes later (at time=15:47) to a position further within the bronchial tree. By ventilating only parts of the lung, the effective FRC was reduced with each advancement of the endotracheal tube.

Figure 5:
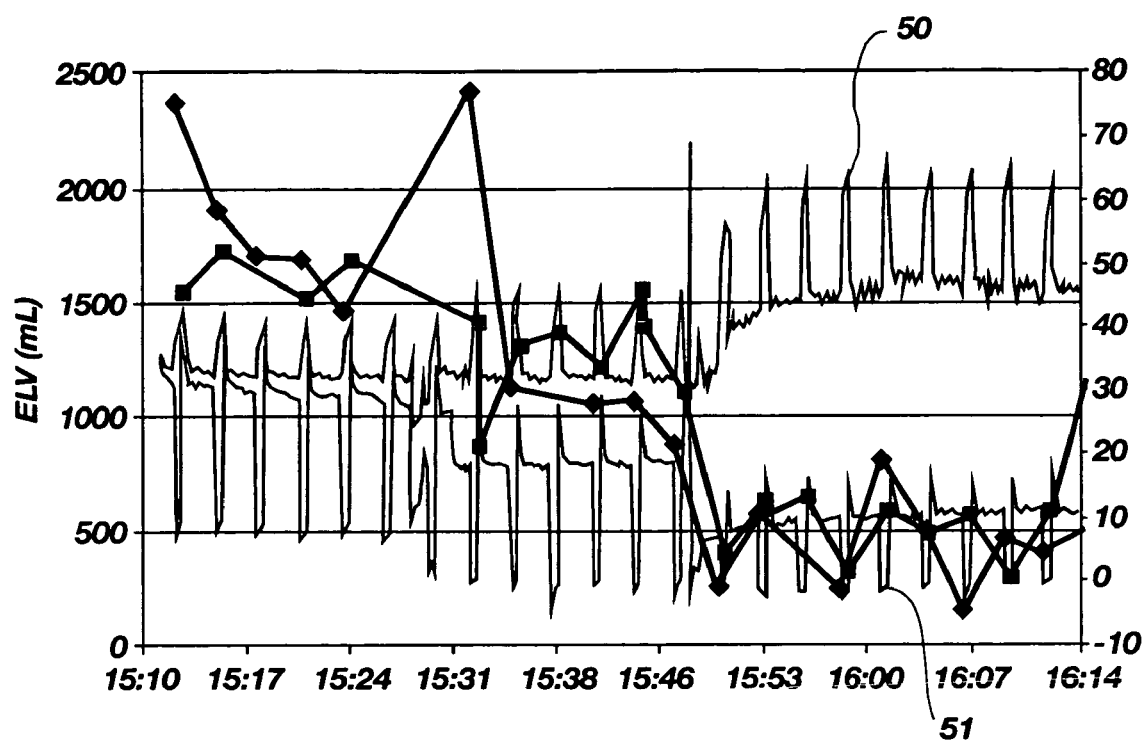
FIG. 5 is a line graph showing the correlation between two sets of ELV calculations that have been made in accordance with teachings of the present invention.

ELV was calculated for various breaths using equation (18). ELV values that were calculated when a sufficient $f_{ACO2}(n)-f_{ACO2}(n-1)$ threshold was present and during certain breaths (e.g., the second breath into rebreathing, the first breath of recovery, etc.) were considered valid and are included as data points in the graph of FIG. 5. Notably, the plotted data points represent ELV minus inspiratory tidal volume. ELV values that were calculated from data obtained during transition from normal breathing into rebreathing are shown as diamond-shaped points. ELV values that were calculated from data obtained during the transition from rebreathing to recovery are shown as squares. The closeness of the lines that extend through the two sets of data indicates that the ELV values and, thus, the algorithm (equations (22 and 23)) from which they were calculated provides reasonable ELV values. Notably, the trends of the two sets of ELV calculations decrease, as expected, at times when the endotracheal tube was advanced further into the lungs of the pig. These trends, as well as their magnitude, are confirmed by the underlying $VCO_2$ signals 50 and $p_{etCO2}$ signals 51. Moreover, the ELV estimations remained relatively stable even when severe changes in $p_{etCO2}$ were noted (see the $p_{etCO2}$ trend after 15:50).

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A method for substantially noninvasively estimating effective lung volume of a subject, the method comprising the acts of:

effecting a change in effective ventilation of a subject;
considering a change in the amount of carbon dioxide in gases residing within the alveoli of the subject's lungs from baseline breathing to breathing in which the change in effective ventilation is effected;
considering a change in carbon dioxide elimination from baseline breathing to breathing in which the change in effective ventilation is effected; and
compensating for changes in the amount of carbon dioxide in gases residing within the alveoli that occur during a breath for estimating the effective lung volume of the subject;
wherein the acts of considering the change in the concentration of carbon dioxide, considering the change in carbon dioxide elimination, and compensating for changes in the amount of carbon dioxide comprise employing the following algorithm in processor:

$$\hat{V}_A^* = \frac{1}{f_{ACO2}(n) - f_{ACO2}(n-1)} \cdot \left[ V_M CO_{2PRE} - V_M CO_2(n) - \frac{V_M CO_{2PRE} - V_M CO_{2DUR}}{p_{ACO2DUR} - p_{ACO2PRE}} \cdot (p_{ACO2}(n) - p_{ACO2PRE}) \right]$$

where $\hat{V}_A^*$ represents the effective lung volume, $f_{ACO2}(n)$ and $f_{ACO2}(n-1)$ represent the concentration of carbon dioxide during successive breaths, only one of which occurs when a change effective ventilation has been effected, $V_M CO_{2\ PRE}$ represents the carbon dioxide elimination measured at or near the mouth of the subject during baseline breathing, $V_M CO_2(n)$ represents the carbon dioxide elimination measured for breath (n), $V_M CO_{2\ DUR}$ represents the carbon dioxide elimination measured at or near the mouth when the change in effective ventilation has been effected, $p_{ACO2\ PRE}$ represents the partial pressure of carbon dioxide within the alveoli of the subject's lung during baseline breathing, and $p_{ACO2}(n)$ represents the partial pressure of carbon dioxide within the alveoli during breath (n).

2. The method of claim 1, wherein the act of compensating comprises the act of:

considering the change in carbon dioxide delivered to a lung from blood as a result of the change in effective ventilation that was effected.

3. The method of claim 2, wherein the act of compensating further comprises the act of:

considering a magnitude of the change in the amount of carbon dioxide in the alveoli from baseline breathing to breathing in which the change in effective ventilation is effected.

4. The method of claim 1, wherein the act of effecting includes the act of rebreathing.

5. The method of claim 1, wherein effecting the act of includes the act of breath holding.

6. A method for substantially noninvasively estimating effective lung volume of a subject, the method comprising the acts of:

effecting a change in effective ventilation of a subject;
considering a change in the amount of carbon dioxide in gases residing within the alveoli of the subject's lungs from baseline breathing to breathing in which the change in effective ventilation is effected;
considering a change in carbon dioxide elimination from baseline breathing to breathing in which the change in effective ventilation is effected; and
compensating for changes in the amount of carbon dioxide in gases residing within the alveoli that occur during a breath for estimating the effective lung volume of the subject;
wherein considering the change in the concentration of carbon dioxide, considering the change in carbon dioxide elimination, and compensating for changes in the amount of carbon dioxide comprise employing the following algorithm in a processor:

$$\hat{V}_A^* = \frac{1}{f_{ACO2}(n) - f_{ACO2}(n-1)} \cdot \left[ V_M CO_{2PRE} - V_M CO_2(n) - PCBF \cdot S_{CO2} \cdot \frac{1}{RR} \cdot (p_{ACO2}(n) - p_{ACO2PRE}) \right],$$

where $\hat{V}_A^*$ represents the effective lung, $f_{ACO2}(n)$ and $f_{ACO2}(n-1)$ represent the concentration of carbon dioxide during successive breaths, only one of which occurs when a change effective ventilation has been effected, $V_M CO_{2\ PRE}$ represents the carbon dioxide elimination measured at or near the mouth of the subject during baseline breathing, $V_M CO_2(n)$ represents the carbon dioxide elimination measured for breath (n), PCBF represents the pulmonary capillary blood flow of the subject, $s_{CO2}$ represents the slope of a standard carbon dioxide dissociation curve, PR represents the subject's respiratory rate, $p_{ACO2\ PRE}$ represents the partial pressure of carbon dioxide within the alveoli of the subject's lung during baseline breathing, and $p_{ACO2}(n)$ represents the partial pressure of carbon dioxide within the alveoli during breath (n).

7. Apparatus for substantially noninvasively estimating effective lung volume of a subject, comprising:

means for effecting a change in effective ventilation of a subject while the subject continues to breathe;
means for considering a change in a concentration of carbon dioxide in gases residing within the alveoli of the subject's lungs from baseline breathing to breathing in which the change in effective ventilation is effected; and
means for considering a change in carbon dioxide elimination from baseline breathing to breathing in which the change in effective ventilation is effected for estimating the effective lung volume of the subject;
wherein the means for considering the change in concentration and considering the change in carbon dioxide elimination comprise means for employing the following algorithm:

$$\hat{V}_A^* = \frac{1}{f_{ACO2}(n) - f_{ACO2}(n-1)} \cdot [V_M CO_{2PRE} - V_M CO_2(n)],$$

where $\hat{V}_A^*$ represents the effective lung volume, $f_{ACO2}(n)$ and $f_{ACO2}(n-1)$ represent the concentration of carbon dioxide during successive breaths, only one of which occurs when a change effective ventilation has been effected, $V_MCO_{2\ PRE}$ represents the carbon dioxide elimination measured at or near the mouth of the subject during baseline breathing, and $V_MCO_2(n)$ represents the carbon dioxide elimination measured for breath (n).

8. The apparatus of claim 7, wherein the means for effecting includes means for effecting rebreathing.

9. Apparatus for substantially noninvasively estimating effective lung volume of a subject, comprising:
   means for effecting a change in effective ventilation of a subject;
   means for considering a change in a concentration of carbon dioxide in gases residing within alveoli of the subject's lungs from baseline breathing to breathing in which the change in effective ventilation is effected; and
   means for considering a change in carbon dioxide elimination from baseline breathing to breathing in which the change in effective ventilation is effected; and
   means for compensating for changes in the amount of carbon dioxide in gases residing within the alveoli that occur during a breath for estimating the effective lung volume of the subject;
   wherein means for considering the change in the concentration of carbon dioxide, the means for considering the change in carbon dioxide elimination, and the means for compensating for changes in the amount of carbon dioxide comprise means for employing the following algorithm:

$$\hat{V}_A^* = \frac{1}{f_{ACO2}(n) - f_{ACO2}(n-1)} \cdot \left[ V_M CO_{2PRE} - V_M CO_2(n) - \frac{V_M CO_{2PRE} - V_M CO_{2DUR}}{p_{ACO2DUR} - p_{ACO2PRE}} \cdot (p_{ACO2}(n) - p_{ACO2PRE}) \right]$$

where $\hat{V}_A^*$ represents the effective lung volume, $f_{ACO2}(n)$ and $f_{ACO2}(n-1)$ represent the concentration of carbon dioxide during successive breaths, only one of which occurs when a change effective ventilation has been effected, $V_MCO_{2\ PRE}$ represents the carbon dioxide elimination measured at or near the mouth of the subject during baseline breathing, $V_MCO_2(n)$ represents the carbon dioxide elimination measured for breath (n), $V_MCO_{2\ DUR}$ represents the carbon dioxide elimination measured at or near the mouth when the change in effective ventilation has been effected, $p_{ACO2\ PRE}$ represents the partial pressure of carbon dioxide within the alveoli of the subject's lung during baseline breathing, and $p_{ACO2}(n)$ represents the partial pressure of carbon dioxide within the alveoli during breath (n).

10. The apparatus of claim 9, wherein the means for compensating comprises:
   means for considering the change in carbon dioxide delivered to a lung from blood as a result of the change in effective ventilation that was effected.

11. The apparatus of claim 10, wherein the means for compensating comprise:
   means for considering a magnitude of the change in the amount of carbon dioxide in the alveoli from baseline breathing to breathing in which the change in effective ventilation is effected.

12. The apparatus of claim 9, wherein means for effecting includes means for rebreathing.

13. The apparatus of claim 9, wherein means for effecting includes means for effecting breath holding.

14. Apparatus for substantially noninvasively estimating effective lung volume of a subject, comprising:
   means for effecting a change in effective ventilation of a subject;
   means for considering a change in a concentration of carbon dioxide in gases residing within alveoli of the subject's lungs from baseline breathing to breathing in which the change in effective ventilation is effected; and
   means for considering a change in carbon dioxide elimination from baseline breathing to breathing in which the change in effective ventilation is effected; and
   means for compensating for changes in the amount of carbon dioxide in gases residing within the alveoli that occur during a breath for estimating the effective lung volume of the subject;
   wherein the means for considering the change in the concentration of carbon dioxide, the means for considering the change in carbon dioxide elimination, and the means for compensating for changes in the amount of carbon dioxide comprise means for employing the following algorithm:

$$\hat{V}_A^* = \frac{1}{f_{ACO2}(n) - f_{ACO2}(n-1)} \cdot \left[ V_M CO_{2PRE} - V_M CO_2(n) - PCBF \cdot S_{CO2} \cdot \frac{1}{RR} \cdot (p_{ACO2}(n) - p_{ACO2PRE}) \right],$$

Where $\hat{V}_A^*$ represents the effective lung volume, $f_{ACO2}(n)$ and $f_{ACO2}(n-1)$ represent the concentration of carbon dioxide during successive breaths, only one of which occurs when a change effective ventilation has been, $V_MCO_{2\ PRE}$ represents the carbon dioxide elimination measured at or near the mouth of the subject during baseline breathing, $V_MCO_2(n)$ represents the carbon dioxide elimination measured for breath (n), PCBF represents the pulmonary capillary blood flow of the subject, $s_{CO2}$ represents the slope of a standard carbon dioxide dissociation curve, RR represents the subject's respiratory rate, $p_{ACO2\ PRE}$ represents the partial pressure of carbon dioxide within the alveoli of the subject's lung during baseline breathing, and $p_{ACO2}(n)$ represents the partial pressure of carbon dioxide within the alveoli during breath (n).

15. Apparatus for substantially noninvasively estimating effective lung volume of a subject, comprising:
   means for effecting a change in effective ventilation of a subject while the subject continues to breathe;
   means for considering a change in the a concentration of carbon dioxide in gases residing within the alveoli of the subject's lungs from baseline breathing to breathing in which the change in effective ventilation is effected; and
   means for considering a change in carbon dioxide elimination from baseline breathing to breathing in which the change in effective ventilation is effected for estimating the effective lung volume of the subject;
   wherein the means for considering the change in the concentration of carbon dioxide, the means for considering the change in carbon dioxide elimination, and the means for compensating for changes in the amount of carbon dioxide comprise means for employing the following algorithm:

$$\hat{V}_A^* = \frac{1}{f_{ACO2}(n) - f_{ACO2}(n-1)} \cdot \left[ V_M CO_{2PRE} - V_M CO_2(n) - \right.$$

-continued
$$PCBF \cdot S_{CO2} \cdot \frac{1}{RR} \cdot (p_{ACO2}(n) - p_{ACO2\ PRE})\Bigg],$$

Where $\hat{V}_A^*$ represents the effective lung volume, $f_{ACO2}(n)$ and $f_{ACO2}(n-1)$ represent the concentration of carbon dioxide during successive breaths, only one of which occurs when a change effective ventilation has been effected, $V_M CO_{2\ PRE}$ represents the carbon dioxide elimination measured at or near the mouth of the subject during baseline breathing, $V_M CO_2(n)$ represents the carbon dioxide elimination measured for breath (n), PCBF represents the pulmonary capillary blood flow of the subject, $s_{CO2}$ represents the slope of a standard carbon dioxide dissociation curve, RR represents the subject's respiratory rate, $p_{ACO2\ PRE}$ represents the partial pressure of carbon dioxide within the alveoli of the subject's lung during baseline breathing, and $p_{ACO2}(n)$ represents the partial pressure of carbon dioxide within the alveoli during breath (n).

* * * * *